United States Patent
Han et al.

(10) Patent No.: US 9,297,747 B2
(45) Date of Patent: Mar. 29, 2016

(54) METHOD TO DETERMINE TRACE AMOUNTS OF CRUDE OIL BY SPECTROSCOPIC ABSORPTION

(71) Applicant: Saudi Arabian Oil Company, Dhahran (SA)

(72) Inventors: Ming Han, Dhahran (SA); Ali Abdallah Al-Yousef, Dhahran (SA); Salah Hamad Al-Saleh, Dhahran (SA); Mohammed Ali AlGeer, Dhahran (SA); Abdullah Alboqmi, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 231 days.

(21) Appl. No.: 13/945,309

(22) Filed: Jul. 18, 2013

(65) Prior Publication Data
US 2015/0021490 A1    Jan. 22, 2015

(51) Int. Cl.
*G01N 21/33*    (2006.01)
*G01N 33/28*    (2006.01)
*G01N 33/18*    (2006.01)
(Continued)

(52) U.S. Cl.
CPC ............... *G01N 21/33* (2013.01); *B01D 11/00* (2013.01); *G01N 1/4055* (2013.01); *G01N 33/1833* (2013.01); *G01N 33/26* (2013.01); *G01N 33/28* (2013.01); *G01N 1/38* (2013.01); *G01N 2001/4061* (2013.01); *G01N 2015/0693* (2013.01)

(58) Field of Classification Search
CPC ............. G01N 21/33; G01N 21/3577; G01N 33/1833; G01N 33/26; G01N 2021/3595
USPC .......................................................... 250/372
See application file for complete search history.

(56) References Cited

U.S. PATENT DOCUMENTS 2,527,121 A    10/1950    Dudenbostel, Jr.
2,767,320 A    10/1956    Coggeshall et al.
(Continued)

FOREIGN PATENT DOCUMENTS

WO    2007/089154 A1    8/2007

OTHER PUBLICATIONS

PCT The International Search Report and The Written Opinion of the International Searching Authority dated Oct. 31, 2014; International Application No. PCT/US2014/046817; International Fiie Date: Jul. 16, 2014.
(Continued)

*Primary Examiner* — David Porta
*Assistant Examiner* — Jeremy S Valentiner
(74) *Attorney, Agent, or Firm* — Bracewell LLP; Constance Gall Rhebergen

(57) ABSTRACT

The present invention relates to a method for determining trace amounts of crude oil in water, including the steps of collecting a sample of an oil-containing fluid, adding a toluene extraction volume to the sample, perturbing the sample, dissolving substantially all of the amount of oil in the toluene extraction volume to create a mixed sample, extracting the mixed sample to create an oil-in-toluene layer and an aqueous fluid layer, removing a portion of the oil-in-toluene layer into a dilution container, diluting the portion of the oil-in-toluene layer with a toluene dilution volume to create a dilute sample, measuring an absorption value of the dilute sample using a spectrophotometer, and comparing the absorption value to a calibration curve to quantify the amount of oil in the oil-containing fluid.

17 Claims, 6 Drawing Sheets

(51) Int. Cl.
*G01N 33/26* (2006.01)
*B01D 11/00* (2006.01)
*G01N 1/40* (2006.01)
G01N 1/38 (2006.01)
G01N 15/06 (2006.01)

(56) References Cited

U.S. PATENT DOCUMENTS

| | | | | |
|---|---|---|---|---|
| 3,468,789 | A | * | 9/1969 | Balassa ................... 208/188 |
| 4,146,799 | A | | 3/1979 | Pitt et al. |
| 4,313,086 | A | * | 1/1982 | Baum ...................... 324/693 |
| 5,076,909 | A | * | 12/1991 | Overfield et al. .......... 208/177 |
| 5,266,800 | A | | 11/1993 | Mullins |
| 5,272,346 | A | * | 12/1993 | Kaplan et al. ............. 250/373 |
| 5,301,536 | A | * | 4/1994 | Ortega et al. .............. 73/31.07 |
| 5,304,807 | A | * | 4/1994 | Lin ........................... 250/373 |
| 5,331,156 | A | | 7/1994 | Hines et al. |
| 5,561,065 | A | | 10/1996 | Schabron |
| 5,679,574 | A | | 10/1997 | Friedman et al. |
| 6,117,682 | A | | 9/2000 | Lynn et al. |
| 6,794,864 | B2 | | 9/2004 | Mirotchnik et al. |
| 6,946,837 | B2 | | 9/2005 | Sorland |
| 7,403,292 | B2 | | 7/2008 | Tomaru |
| 7,482,811 | B2 | | 1/2009 | Freedman |
| 2011/0194105 | A1 | * | 8/2011 | LaFrancois et al. ......... 356/300 |
| 2014/0375991 | A1 | * | 12/2014 | Schneider ............. G01N 31/16 356/326 |
| 2015/0106034 | A1 | * | 4/2015 | Koseoglu et al. .............. 702/25 |

OTHER PUBLICATIONS

Patel, M. S.: Rapid and Convenient Laboratory Method for Extraction and Subsequent Spectrophotometric Determination of Bitumen Content of Bituminous Sands; Analytical Chemistry; May 1, 1974; pp. 794-795; vol. 46, No. 6; XP002731074.

Elraies, K.A., Tan, I.M. and Awang, M., "A New Approach to Low-Cost, High Performance Chemical Flooding System," SPE 133004, SPE Production and Operations Conference and Exhibition, Tunis, Tunisia, Jun. 8-10, 2010, Society of Petroleum Engineers.

Taber, J.J., Kamath, I.S.K. and Reed, R.L., "Mechanism of Alcohol Displacement of Oil from Porous Media," Society of Petroleum Engineers Journal, Sep. 1961: pp. 195-212.

Torsaeter, O., Boe, R. and Holt, T. "An Experimental Study of the Relationship Between Rock Surface Properties, Weltability and Oil Production Characteristics." SCA-9739, International Symposium of Society of Core Analysts, Calgary, Alberta, Canada, Sep. 7-10, 1997.

Product Brochure—OCMA-350 Oil Content Analyzer at http://www.horiba.com/process-environmental/products/water-quality-measurement/lab-use/details/ocma-350-oil-content-monitor-356/.

* cited by examiner

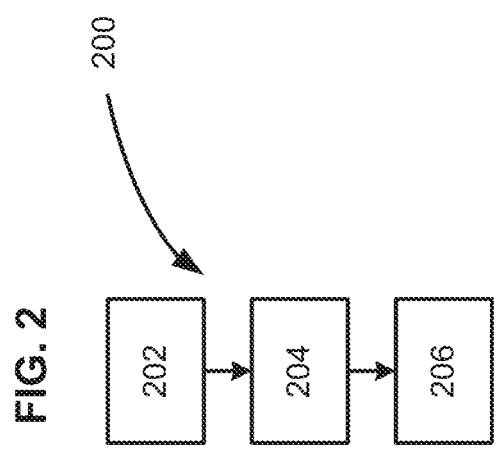

METHOD TO DETERMINE TRACE AMOUNTS OF CRUDE OIL BY SPECTROSCOPIC ABSORPTION

FIELD OF THE INVENTION

This invention relates to a method to determine trace amounts of crude oil by spectroscopic absorption. More specifically, the present invention relates to a method to quantify the amount of oil in an oil-containing fluid.

BACKGROUND OF THE INVENTION

Analytical testing for the amount of oil in a sample from coreflooding (water, $CO_2$, or chemical) is an important step in determining the success of oil recovery. Oil in coreflooding can be present as an emulsion, an oil-water mixture, or in a clear oil phase, where the oil may be present in trace amounts. Determining the amount of oil in an oil-water mixture can be accomplished using a variety of common analytical methods. Common analytical methods include visual observation, near infra-red reflectance (NIR) spectroscopy, nuclear magnetic resonance (NMR), an OCMA-300 series oil content analyzer, and absorption spectroscopy.

Visual observation involves a sample of the oil-water mixture placed in a graduated cylinder and allowed to separate into an oil phase and a water phase. The amount of oil is then determined based on the height of the oil phase in the graduated cylinder. Visual observation is inaccurate when the amount of oil is less than 0.1 ml.

NIR spectroscopy requires a special instrument for the measurement and is sensitive to the changes in the texture of the samples. NMR also requires specialized equipment for measurement. An OCMA-300 series oil content analyzer can be used for measuring the oil content in emulsion samples. These methods all suffer from major drawbacks. First, they require expensive, complicated equipment and skilled operators, which adds to the expense of running a sample. Second, the methods can only be run on emulsion samples, not other samples of trace amounts of oil in water. Third, these methods can take significant time to obtain results on a given sample.

SUMMARY OF THE INVENTION

The present invention relates to a method for determining trace amounts of crude oil in an oil-containing fluid within a core sample, including the steps of removing at least a portion of the oil-containing fluid from the core sample to create a sample of oil-containing fluid, where the oil-containing fluid includes an amount of oil and an aqueous fluid, adding a toluene extraction volume to the sample, perturbing the sample, such that the toluene extraction volume contacts the oil-containing fluid, dissolving substantially all of the amount of oil in the toluene extraction volume to create a mixed sample, extracting the mixed sample to create an oil-in-toluene layer and an aqueous fluid layer, removing a pre-defined portion of the oil-in-toluene layer into a dilution container, diluting the pre-defined portion of the oil-in-toluene layer with a toluene dilution volume to create a dilute sample, measuring an absorption value of the dilute sample using a spectrophotometer, and comparing the absorption value to a calibration curve to quantify the amount of oil in the oil-containing fluid.

In certain embodiments of the present invention, the method further includes the step of separating the mixed sample to separate the oil-in-toluene layer from the aqueous fluid layer. In certain embodiments, the oil-containing fluid includes water, coreflood effluent, high water-cut field produced water, or combinations thereof. In certain embodiments, the oil-containing fluid includes a plurality of oil drops on the walls of a sample container, where the sample is placed in the sample container during the step of collecting a sample. In certain embodiments, the oil-containing fluid includes an oil-in-water emulsion. In certain embodiments, the toluene extraction volume is substantially pure toluene. In certain embodiments, the toluene dilution volume is substantially pure toluene. In certain embodiments, the step of separating the mixed sample is carried out by using a separating funnel. In certain embodiments, the step of measuring the absorption value of the oil-in-toluene layer is performed using a spectrophotometer in the wavelength range of between about 280 nm to 400 nm.

The present invention also relates to a method for determining trace amounts of crude oil in water, including the steps of collecting a sample of an oil-containing fluid, where the oil-containing fluid includes an amount of oil and an aqueous fluid, adding a toluene extraction volume to the sample, perturbing the sample, where the toluene extraction volume contacts the oil-containing fluid, dissolving substantially all of the amount of oil in the toluene extraction volume to create a mixed sample, extracting the mixed sample to create an oil-in-toluene layer and an aqueous fluid layer, separating the mixed sample to separate the oil-in-toluene layer and the aqueous fluid layer, removing a pre-defined portion of the oil-in-toluene layer into a dilution container, diluting the pre-defined portion of the oil-in-toluene layer with a toluene dilution volume to create a dilute sample, measuring an absorption value of the dilute sample using a spectrophotometer, and comparing the absorption value to a calibration curve to quantify the amount of oil in the oil-containing fluid.

In certain embodiments, the oil-containing fluid includes water, coreflood effluent, high water-cut field produced water, or combinations thereof. In certain embodiments, the oil-containing fluid includes a plurality of oil drops on the walls of a sample container, where the sample is placed in the sample container during the step of collecting a sample. In certain embodiments, the oil-containing fluid includes an oil-in-water emulsion. In certain embodiments, the toluene extraction volume is substantially pure toluene. In certain embodiments, the toluene dilution volume is substantially pure toluene. In certain embodiments, the step of separating the mixed sample is carried out by separating funnel. In certain embodiments, the step of measuring the absorption value of the oil-in-toluene layer is performed using a spectrophotometer in the wavelength range of between about 280 nm to 400 nm.

BRIEF DESCRIPTION OF THE DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

FIG. 2 depicts a flowchart for a method for developing a calibration curve for use in method 100.

DETAILED DESCRIPTION

While the invention will be described with several embodiments, it is understood that one of ordinary skill in the relevant art will appreciate that many examples, variations and alterations to the apparatus and methods described herein are within the scope and spirit of the invention. Accordingly, the exemplary embodiments of the invention described herein are set forth without any loss of generality, and without imposing limitations, on the claimed invention.

Figure 1:
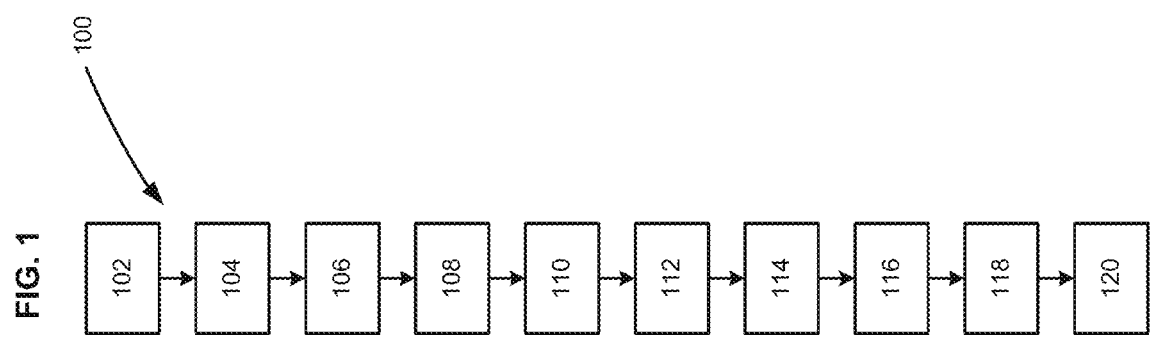
FIG. 1 depicts a flowchart for a method for the determination of trace amounts of oil using spectroscopic absorption according to one embodiment of the present invention.

FIG. 1 depicts method 100 for determining trace amounts of oil using spectroscopic absorption. In sample collection step 102, a sample of an oil-containing fluid is collected in a sample container. The oil-containing fluid can be any oil-containing fluid that includes an amount of oil and an aqueous fluid. Any miscible or immiscible oil-containing fluid can be collected including an oil-containing fluid with separate oil and aqueous phases (immiscible), clear oil phase fluid (immiscible), an oil-in-water type emulsion fluid (miscible) or a water-in-oil type emulsion fluid (miscible). A clear oil phase occurs when the amount of oil is too small for visual observation or is adhered to the tube wall. The sample can be from any source of oil-containing fluid. In some embodiments, the sample can be collected from the effluent of coreflooding tests, coreflood displacement test, or high water-cut field produced water. In at least one embodiment of the present invention, the oil-containing fluid is removed from a core sample. In at least one embodiment of the present invention, the volume of the sample does not need to be recorded as it will not be used in calculations or determinations relevant to determining the amount of oil in the oil-containing fluid.

In toluene addition step 104, a toluene extraction volume is added to the sample collected in sample collection step 102 to produce a total sample. The toluene used in method 100 for determining trace amounts of oil using spectroscopic absorption is a pure or substantially pure toluene, such as ACS Grade Toluene. The toluene extraction volume added to the sample container is determined based on the size of sample. The toluene amount to be added is determined based on estimations of expected amounts of residual crude oil in the sample and expected characterization of that crude oil based on actual operating data collected from the site, for reservoirs where at least primary recovery has been undertaken or where it has been simulated in a coreflooding displacement test. The volume of the toluene extraction volume is recorded.

Once the toluene extraction volume is added in toluene addition step 104, the sample container is perturbed in perturbation step 106. In at least one embodiment of the present invention, perturbation step 106 is a gentle perturbation. Perturbation step 106 causes the toluene extraction volume to contact the oil in the oil-containing fluid. Perturbation step 106 allows the toluene to mix with the oil-containing fluid, but should not be so forceful an agitation as to cause formation of a water-in-oil emulsion. Exemplary perturbation methods include gently shaking the sample container, swirling the sample container, inverting the sample container, pulsing the sample container, or any other agitation method that would cause the toluene to contact the oil-containing fluid without formation of a water-in-oil emulsion.

Perturbation step 106 initiates dissolution step 108, where the toluene extraction volume dissolves the oil in the oil-containing fluid to create a mixed sample. The toluene dissolves both oil drops adhered to the wall of the sample container and the oil in the oil-containing fluid to create the mixed sample. Once all, or substantially all, of the oil is dissolved in the toluene extraction volume in dissolution step 108, the mixed sample in the sample container is undisturbed for extraction step 110. In extraction step 110, the dissolved oil-in-toluene separates from the aqueous fluid forming a two-phase solution, an aqueous fluid layer including the aqueous fluid from the oil-containing fluid and an oil-in-toluene layer containing all, or substantially all, of the oil from the oil-containing fluid. Extraction step 110 can take from 30 minutes to 12 hours. Perturbation step 106, dissolution step 108, and extraction step 110 can be repeated until all of the oil is dissolved in the substantially pure toluene. Advantageously, this invention allows for the breaking of any emulsion to allow for appropriate separation of oil-in-toluene layer.

Separation step 112 separates the oil-in-toluene layer from the aqueous fluid layer. Any filtration method capable of separating oil from water can be used. Exemplary separation methods include use of gravity filtration or a separating funnel. In a gravity filtration, a glass funnel with folded filter paper wetted by pure toluene is used. In at least one embodiment of the present invention, separation step 112 is carried out using gravity filtration using quantitative filter paper with a medium porosity wetted in substantially pure toluene. In at least one embodiment of the present invention, method 100 does not include separation step 112. In some embodiments of the present invention, water remains in the oil-in-toluene layer as a water-in-oil emulsion or as a water-in-toluene emulsion after extraction step 110. In embodiments where water remains in the oil-in-toluene layer, separation step 112 includes separation to remove the water-in-oil emulsion from the oil-in-toluene layer using any filtration method capable of separating water-in-oil emulsion from oil. The presence of a water emulsion in the oil-in-toluene makes measurement of the absorption using the spectrophotometer difficult.

After a stable two-phase solution is obtained in extraction step 110 or after separation in separation step 112, a pre-defined portion of the oil-in-toluene layer is removed in portion removal step 114. The pre-defined portion removed is placed in a dilution container, such as a flask or other suitable container. An exemplary pre-defined portion would be 1 cc (ml). Other pre-defined portions are also encompassed within this invention. The pre-defined portion can be removed by pipette or other lab equipment capable of accurate measurement of a volume of liquid. The pre-defined portion removed is a known volume of the oil-in-toluene layer, the volume is determined based on the need for further dilution in dilution step 116. In accordance with at least one embodiment of the present invention, the pre-defined portion removed is 1 ml.

In dilution step 116, the pre-defined portion of the oil-in-toluene layer removed in portion removal step 114 is diluted with a toluene dilution volume. The toluene dilution volume is a pure or substantially pure volume of toluene. The addition of the toluene dilution volume creates a dilute sample. The toluene dilution volume is determined based on the need to further dilute the portion of oil-in-toluene layer obtained in portion removal step 114. In some embodiments, the desired oil concentration is in the range of about 0.01 ml oil per 100 ml toluene to about 0.1 ml oil per 100 ml toluene. In an alternate embodiment of the present invention, the oil concentration in the pre-defined portion removed in portion removal step 114 is below about 0.1 ml per 100 ml toluene and dilution step 116 is not needed. A sight test is used to estimate how much toluene to add for dilution. In the sight test, visual observation is used to compare the portion removed with a known oil-in-toluene sample to determine if the portion removed needs further dilution. If the pre-defined portion removed appears more concentrated than the known sample, additional toluene dilution volume is added. The known oil-in-toluene sample can be created for this purpose, or may be from the samples created for the calibration curve in method 200 described herein. In at least one embodiment of the present invention, dilution step 116 is repeated until the oil concentration is less than 0.01 ml oil per 100 ml toluene or until the pre-defined portion appears more dilute than the known sample. The total toluene dilution volume added is recorded.

Figure 5:
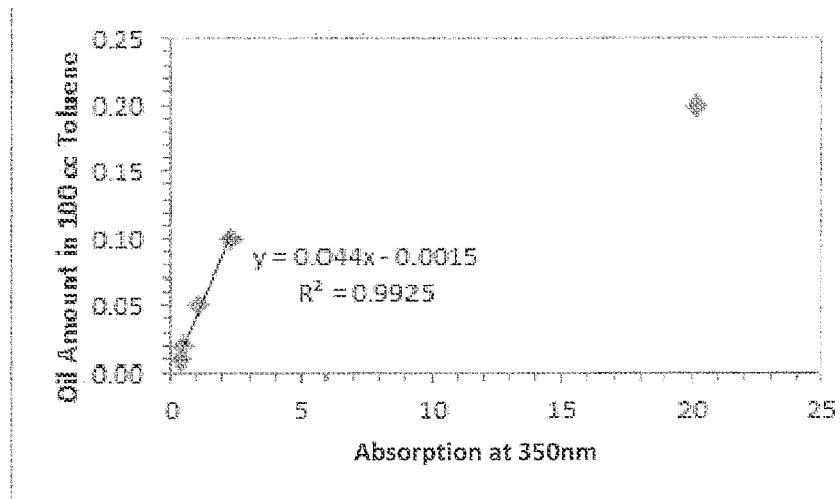
FIG. 5 is a graph of a calibration curve.

In measuring step 118, a measured portion of the dilute sample is placed in a spectrophotometer and an absorption value is measured by means of absorption spectroscopy. The measured portion is withdrawn from the dilute sample using a pipette. The size of the measured portion is 1 ml. Absorption spectroscopy quantifies the amount of a substance present in a sample by subjecting the sample to a specific light wavelength, in one embodiment of the present invention, the absorption value is measured using light wavelengths in the range of 280 nm to 400 nm. The specific wavelength used in measuring step 118 corresponds to the wavelength used to create the calibration curve described herein with reference to FIG. 2. Light between 280 nm and 400 nm is ideal because at low oil concentrations a linear relationship exists between absorption and concentration according to the Beer-Lambert law. FIG. 5 depicts a calibration curve, showing the linear relationship when the amount of oil in 100 ml toluene is between 0.01 ml oil and 0.1 ml oil. Below 280 nm, the absorption does not show a linear relationship with concentration. Above 400 nm, the absorption measures the same value as that of toluene.

Once an absorption value is determined from measuring step 118, the absorption value is used in comparison step 120 to determine a corresponding amount from the calibration curve, described herein with reference to FIG. 2. The corresponding amount is a quantity of oil. The calibration curve relates corresponding amount with absorption value. For a measured absorption value, the corresponding amount can be determined using the linear regression equation calculated from the calibration curve.

FIG. 2 depicts calibration method 200 describing how to create a calibration curve for use in comparison step 120. In at least one embodiment of the present invention, calibration method 200 is performed prior to method 100 for determining trace amounts of oil using spectroscopic absorption. In at least one embodiment of the present invention, calibration method 200 is performed for each production well at the time the coreflood test is performed. Preparing a calibration curve for each production well at the time of the coreflood test ensures the oil type to be quantified is represented on the calibration curve. Additionally, a crude oil's property could change as a function of time after it is produced from the production well, so performing calibration method 200 close in time to the test ensures that the calibration curve is representative of the oil in the samples collected in sample collection step 102.

In sample creation step 202, a series of calibration samples are prepared. For each calibration sample, a calibration toluene volume is added to a known volume of oil to get a total calibration sample. The known volume of oil is the same type of oil collected in sample collection step 102. The number of calibration samples created depends on factors including the type of sample collected in sample collection step 102, the desired accuracy of the calibration curve, or the number of samples collected in sample collection step 102. An example of a calibration sample includes adding 0.005 ml oil to 100 ml toluene. Another example includes adding 0.10 ml oil to 100 ml toluene. In accordance with at least one embodiment of the present invention, calibration samples are prepared where the known quantity of oil is in the range of about 0.005 ml to about 0.20 ml oil, alternately from about 0.005 ml to about 0.010 ml, alternately from about 0.010 ml to about 0.015 ml, alternately from about 0.015 ml to about 0.02 ml, alternately from about 0.02 ml to about 0.03 ml, alternately from about 0.03 ml to about 0.04 ml, alternately from about 0.04 ml to about 0.05 ml, alternately from about 0.05 ml to about 0.06 ml, alternately from about 0.06 ml to about 0.07 ml, alternately from about 0.07 ml to about 0.08 ml, alternately from about 0.08 ml to about 0.09 ml, alternately from about 0.09 ml to about 0.10 ml, alternately from about 0.10 nil to about 0.20 ml.

In mix step 204, the calibration samples are perturbed as described with reference to perturbation step 106. In one embodiment of the present invention, the calibration samples are swirled in the sample container to encourage complete mixing or dissolution of the oil in the toluene.

Once mixed, the absorption value of each calibration sample is measured using a spectrophotometer in measuring step 206. The calibration samples created in sample creation step 202 are subjected to different wavelengths in the range of 280 nm to 400 nm. For each wavelength, an absorption value of the calibration sample is measured. A calibration curve for each wavelength is created as a plot of absorption value versus known quantity of oil. The plot which exhibits the Beer-Lambert law linear relationship between absorption value and quantity of oil is the wavelength that will be used in measuring step 118.

In at least one embodiment of the present invention, method 200 occurs before method 100.

In at least one embodiment of the present invention, method 100 occurs in the absence of fluid (gas or liquid) assistance to move the sample from one step to the next. In an alternate embodiment of the present invention, no fluids are introduced to the sample container before the sample collected in sample collection step 102 is introduced to the sample container. In accordance with an embodiment of the present invention, no fluids are introduced to the dilution container before the portion of oil-in-toluene obtained in portion removal step 114 is introduced.

In at least one embodiment of the present invention, method 100 is capable of measuring a range from about 100 ppm volume oil in toluene to about 2,000 ppm volume oil in toluene. Method 100 provides a method to determine the absolute oil amount produced from the coreflood or in place in the surrounding reservoir. In accordance with at least one embodiment of the present invention, method 100 has an error of less than about 15 volume percent. In an alternate embodiment of the present invention, method 100 has an error of less than 10 volume percent. In an alternate embodiment of the present invention, method 100 has an error of less than 5 volume percent. An error of 10 volume percent translates to an absolute error in the range between about 0.001 ml and 0.005 ml. In certain embodiments, method 100 occurs in the absence of a measurement of the components of the oil phase. In exemplary embodiments of method 100, measuring step 118 only quantities the total amount of oil in the sample, but does not indicate the separate components (or their quantities) of the oil.

Exemplary sample containers useful for the present invention include a test tube, flask, bottle, graduated cylinder, or any other container capable of holding a volume of an oil-containing fluid. The size of the sample container is determined based on the total sample volume, that is the sample of oil-containing fluid and the toluene extraction volume. In at least one embodiment of the present invention, the size of the sample container is larger than the total sample volume. Exemplary dilution containers useful for the present invention include a test tube, flask, bottle, graduated cylinder, or any other container capable of holding a volume of an oil-containing fluid. The size of the dilution container is determined based on the volume of the dilute sample, that is the dilution portion and the toluene dilution volume. In at least one embodiment of the present invention, the size of the dilution container is larger than the volume of the dilute sample. In at least one embodiment of the present invention, the toluene used is a pure or substantially pure toluene, such as ACS Grade Toluene. Portion removal step 114 can be accomplished using a pipette, syringe, or other laboratory tool that can accurately measure a volume, such that the volume of the portion removed is known. In at least one embodiment of the present invention, the spectrophotometer used is Mode 2800, UNICO. In an alternate embodiment of the present invention, the spectrophotometer is a CARY 5000 UV-VIS-NIR Spectrophotometer made by Agilent. One of ordinary skill in the art will appreciate that any spectrophotometer capable of measuring an absorption value in the light wavelength of 280 nm to 400 nm can be used in the present invention.

In accordance with one embodiment of the present invention, method 100 is useful for performing a field test. In accordance with one embodiment of the present invention, a field test kit includes a sample container, a dilution container, pipettes, a portable spectrophotometer, a quantity of toluene sufficient to extract and dilute a sample, and a filter medium and apparatus. A field test kit allows a user to make measurements to determine trace amounts of oil in water in a place other than a laboratory, such as a reservoir field or other facility.

In accordance with an embodiment of the present invention, method 100 and method 200 can be used to determine an oil in place volume in a reservoir. First, core samples are taken at predetermined areas across a pilot area of a zone in a reservoir field. The pilot area can be anywhere from 20 acres to 40 acres. The number of core samples taken depends on the size of the pilot area. In certain embodiments, 100 core samples are pulled. A core sample is subjected to a process that causes the core sample to be subject to conditions simulating the actual behavior of the field during drilling, water flooding, secondary recovery activities, and/or tertiary recovery activities. In accordance with one embodiment of the present invention, the process includes placing the core sample in a vessel with fluid surrounding it. The vessel is then pressurized, heated, and the fluid flows. The process is repeated for each recovery stage: fresh oil, sea water/brine flooding, tertiary recovery methods. In certain embodiments, residual oil will remain in the core sample. In certain embodiments, methods 100 and 200 can be used to estimate the amount of residual oil in the core sample. In certain embodiments, methods can be used to test various tertiary recovery fluids or methods to produce the residual oil from the core sample. The process is repeated for each core sample. Using the estimated amount of residual oil in each core sample, an estimate can be determined for the entire pilot area.

In certain embodiments, methods 100 and 200 can be used to determine which post-tertiary technique would work best in the reservoir.

EXAMPLES

Example 1

| Sample | Oil-Containing Fluid, ml | Total Sample, ml | Portion Removed | Absorption Value at 350 nm | Corresponding Amount, ml | Calculated Amount, ml | % Error |
|---|---|---|---|---|---|---|---|
| 1 | 0.03 | 3.70 | 1.00 | 0.237 | 0.008928 | 0.0330336 | +10.11 |
| 2 | 0.09 | 4.40 | 1.00 | 0.538 | 0.022172 | 0.0975568 | +8.39 |
| 3 | 0.08 | 3.70 | 1.00 | 0.478 | 0.019532 | 0.0722684 | −9.66 |

Figure 3B:
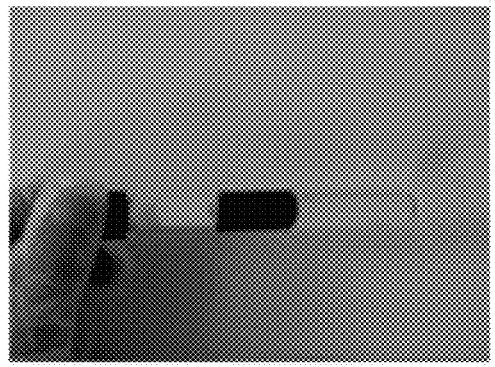
FIG. 3b is a pictorial representation of a two-phase solution containing an oil-in-toluene layer and an aqueous fluid layer.
Figure 3A:
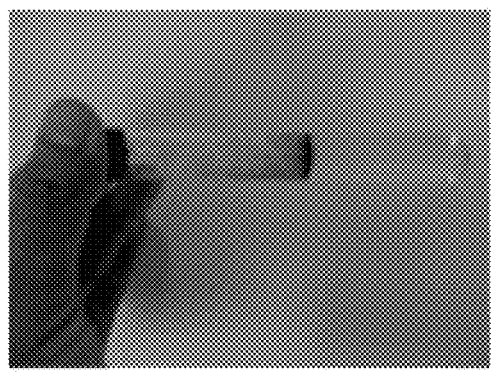
FIG. 3a is a pictorial representation of a clear oil phase.

In Example 1, the sample was a clear oil phase fluid where a known quantity of oil was added to a test tube of water, as depicted in FIG. 3a. Sample 1, the oil-containing fluid was 0.03 ml of Uthmaniyah (UTMN) oil with a density of 0.8720 g/ml at 23° C. in 5 ml. To the sample, a toluene extraction volume was added to create a total sample. In Sample 1, the toluene extraction volume was 3.67 ml of substantially pure toluene to create a total sample of 3.70 ml. The test tube was gently perturbed, the oil was dissolved in the toluene and the oil was extracted resulting in a two-phase solution of an oil-in-toluene layer above an aqueous fluid layer, as depicted in FIG. 3b. No filtration step was performed in this example. A portion of the oil-in-toluene layer was removed. A toluene dilution volume was added to the removed portion of the oil, in sample 1, the portion removed was 1.00 ml and it was mixed with 100 ml of toluene. The absorption value at 350 nm was measured using a spectrophotometer. The absorption value of Sample 1 was 0.237. The absorption value was compared to a calibration curve. The calibration curve used in Example 1 is shown in FIG. 5. The calibration curve shows a linear regression between oil concentrations of 0.01 ml oil in 100 ml toluene and 0.1 ml oil in 100 ml toluene according to the following:

$$\text{Corresponding Amount} \sim 0.044 * \text{Absorption} - 0.0015.$$

Based on the calibration curve, the corresponding amount was determined. In Sample 1, the corresponding amount was 0.008928 ml. To determine the amount of oil in the original sample, the corresponding amount was multiplied by the total sample volume to determine the calculated amount of total oil. The calculated amount in Sample 1 was 0.0330336 ml. The error was calculated to be 10.11 volume percent or an absolute error of 0.003 ml.

Example 2

| Sample | Sample volume, ml | Toluene Extraction Volume, ml | Portion Removed, ml | Toluene Dilution Volume, ml | Absorption Value at 289 nm | Corresponding Amount, ml | Calculated Amount, ml |
|---|---|---|---|---|---|---|---|
| 1 | 50 | 100 | 1.0 | 19 | 1.357 | 0.01655 | 0.331 |

Figure 4B:
FIG. 4b is a pictorial representation of a two-phase solution containing an oil-in-toluene layer and an aqueous fluid layer.
Figure 4A:
FIG. 4a is a pictorial representation of a coreflood effluent sample.

In Example 2, an unknown amount of an oil-containing fluid, a UTMN oil with a density of 0.8720 g/ml at 23° C., as depicted in FIG. 4a, was perturbed, dissolved, and extracted with 100 ml of toluene (toluene extraction volume) to create a two-phase solution of an oil-in-toluene layer and an aqueous fluid layer, as depicted in FIG. 4b. Then, a 1.0 ml portion of the oil-in-toluene layer was removed and further diluted with 19 ml of toluene (toluene dilution volume) to create the dilute sample. The absorption value of the dilute sample was measured using a spectrophotometer at a light wavelength of 289 nm. The absorption value measured was 1.357. For example 2, the correlation between absorption value and the amount of oil as defined by the correlation curve was:

$$\text{Corresponding Amount of Oil} = 0.013046 * \text{absorption value} - 0.0011473$$

An absorption value of 1.357 on the calibration curve results in a corresponding amount of 0.01655 ml, which was multiplied by the dilute sample volume of 20 ml (portion removed plus toluene dilution volume) to get a calculated amount of 0.331 ml of oil.

Example 3

| Sample | Sample Volume, ml | Toluene Extraction Volume, ml | Portion Removed, ml | Dilution Volume, ml | Absorption at 360 nm | Corresponding Amount, ml | Calculated Amount, ml |
|---|---|---|---|---|---|---|---|
| A | 100 | 100 | N/A | N/A | 0.94286 | 0.0309 | 0.0309 |
| B | 100 | 100 | 1 | 4 | 0.57515 | 0.0186 | 0.0928 |
| C | 100 | 100 | 1 | 9 | 0.3525 | 0.0111 | 0.1110 |
| D | 100 | 100 | 1 | 3 | 0.6103 | 0.0197 | 0.0790 |
| E | 100 | 100 | N/A | N/A | 0.9366 | 0.0307 | 0.0307 |
| F | 100 | 100 | 1 | 3 | 0.8396 | 0.0274 | 0.1097 |
| G | 100 | 100 | 1 | 19 | 0.3204 | 0.0100 | 0.2005 |

Figure 6:
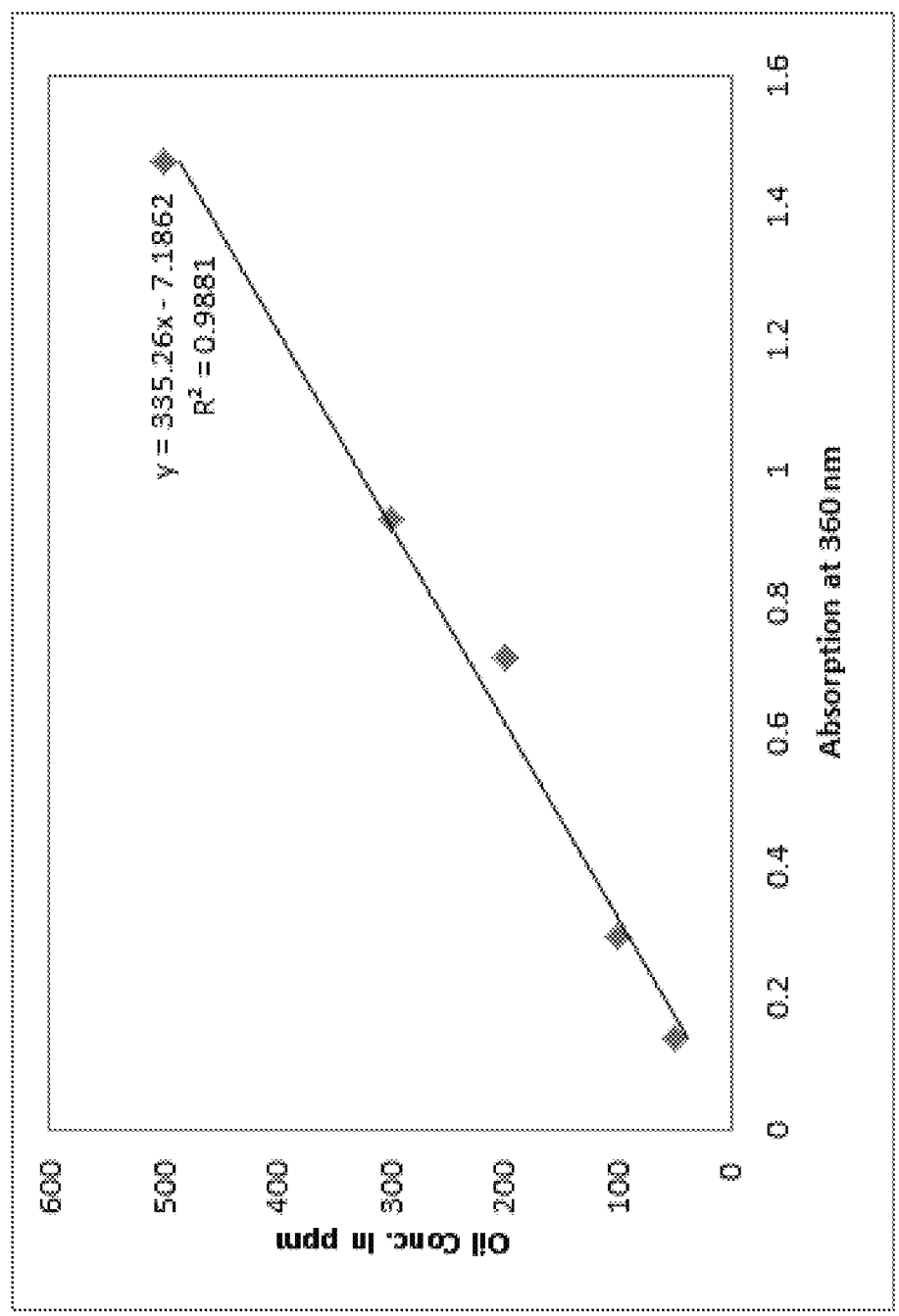
FIG. 6 is a graph of a calibration curve.

In Example 3, a series of samples, representing core samples taken from across a zone in a reservoir field, involving an unknown amount of an oil-containing fluid, a UTMN oil, was perturbed, dissolved, and extracted with 100 ml of toluene (toluene extraction volume). Then, a 1 ml portion of the oil-in-toluene layer was removed and mixed with a toluene extraction volume, if needed. In Samples A and E, the concentration of the oil-in-toluene layer was below 0.1 ml oil in 100 ml toluene based on the sight test, so further dilution was not necessary. In Samples B, C, D, F, and G, the concentration of the oil-in-toluene layer was above 0.1 ml oil in 100 ml toluene so further dilution was necessary. In these samples, a 1.00 ml portion of the oil-in-toluene layer was removed and mixed with a toluene dilution volume. For example, in Sample B the toluene dilution volume was 4 ml, for a dilution sample of 5 ml. The absorption value of the dilution sample was measured by a spectrophotometer at 360 nm. The absorption value of Sample B was 0.57515. The calibration curve for example 3, as depicted in FIG. 6, displayed a linear regression of oil concentration:

$$\text{Corresponding Amount} = (335.26 * \text{absorption value} - 7.1862)/10000.$$

The corresponding amount for Sample B was 0.0186 ml. To determine the amount of oil in the original sample, the corresponding amount was multiplied by the dilution sample to determine the calculated amount. The calculated amount in Sample B was 0.0928 ml.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a," "an," and "the" include plural referents, unless the context clearly dictates otherwise.

Optional or optionally means that the subsequently described event or circumstances can or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

What is claimed is:

1. A method for determining trace amounts of crude oil in an oil-containing fluid within a core sample, the method comprising the steps of:
   removing at least a portion of the oil-containing fluid from the core sample to create a sample of oil-containing fluid in a sample container, wherein the oil-containing fluid comprises an amount of oil and an aqueous fluid;
   adding an extraction volume comprising toluene to the sample in the sample container;
   perturbing the sample in the sample container, wherein the extraction volume comprising toluene contacts the oil-containing fluid;
   dissolving substantially all of the amount of oil in the extraction volume comprising toluene to create a mixed sample in the sample container;
   extracting the mixed sample to create an oil-in-toluene layer and an aqueous fluid layer in the sample container;
   removing a pre-defined portion of the oil-in-toluene layer from the sample container into a dilution container;
   diluting the pre-defined portion of the oil-in-toluene layer with a toluene dilution volume to create a dilute sample;
   measuring an absorption value of the dilute sample using a spectrophotometer; and
   comparing the absorption value to a calibration curve to quantify the amount of oil in the oil-containing fluid, wherein the method for determining trace amounts of crude oil in an oil-containing fluid is in the absence of a fluid assist.

2. The method of claim 1, further comprising the step of separating the mixed sample to separate the oil-in-toluene layer from the aqueous fluid layer.

3. The method of claim 1, wherein the oil-containing fluid comprises water, coreflood effluent, high water-cut field produced water, or combinations thereof.

4. The method of claim 1, wherein the oil-containing fluid comprises a plurality of oil drops on the walls of a sample container, wherein the sample is placed in the sample container during the step of collecting a sample.

5. The method of claim 1, wherein the oil-containing fluid comprises an oil-in-water emulsion.

6. The method of claim 1, wherein the extraction volume comprising toluene is substantially pure toluene.

7. The method of claim 1, wherein the toluene dilution volume is substantially pure toluene.

8. The method of claim 2, wherein the step of separating the mixed sample is carried out by using a separating funnel.

9. The method of claim 1, wherein the step of measuring the absorption value of the oil-in-toluene layer is performed using a spectrophotometer in the wavelength range of between 280 nm to 400 nm.

10. A method for determining trace amounts of crude oil in water, the method comprising the steps of:
    collecting a sample of an oil-containing fluid in a sample container, wherein the oil-containing fluid comprises an amount of oil and an aqueous fluid;
    adding a extraction volume comprising toluene to the sample in the sample container;
    perturbing the sample in the sample container, wherein the extraction volume comprising toluene contacts the oil-containing fluid;
    dissolving substantially all of the amount of oil in the extraction volume comprising toluene to create a mixed sample in the sample container;
    extracting the mixed sample to create an oil-in-toluene layer and an aqueous fluid layer in the sample container;
    separating the mixed sample to separate the oil-in-toluene layer and the aqueous fluid layer in the sample container;
    removing a pre-defined portion of the oil-in-toluene layer into a dilution container;
    diluting the pre-defined portion of the oil-in-toluene layer with a toluene dilution volume to create a dilute sample;
    measuring an absorption value of the dilute sample using a spectrophotometer; and
    comparing the absorption value to a calibration curve to quantify the amount of oil in the oil-containing fluid, wherein the method for determining trace amounts of crude oil in an oil-containing fluid is in the absence of a fluid assist.

11. The method of claim 10, wherein the oil-containing fluid comprises water, coreflood effluent, high water-cut field produced water, or combinations thereof.

12. The method of claim 10, wherein the oil-containing fluid comprises a plurality of oil drops on the walls of a sample container, wherein the sample is placed in the sample container during the step of collecting a sample.

13. The method of claim 10, wherein the oil-containing fluid comprises an oil-in-water emulsion.

14. The method of claim 10, wherein the extraction volume comprising toluene is substantially pure toluene.

15. The method of claim 10, wherein the toluene dilution volume is substantially pure toluene.

16. The method of claim 10, wherein the step of separating the mixed sample is carried out by using a separating funnel.

17. The method, of claim 10, wherein the step of measuring the absorption value of the oil-in-toluene layer is performed using a spectrophotometer m the wavelength range of between 280 nm to 400 nm.

* * * * *